United States Patent
Kim et al.

(10) Patent No.: US 11,427,699 B2
(45) Date of Patent: Aug. 30, 2022

(54) PLASTICIZER COMPOSITION, RESIN COMPOSITION AND METHODS OF PREPARING THE SAME

(71) Applicant: LG CHEM, LTD., Seoul (KR)

(72) Inventors: Hyun Kyu Kim, Daejeon (KR); Mi Yeon Lee, Daejeon (KR); Yun Ki Cho, Daejeon (KR); Jeong Ju Moon, Daejeon (KR); Joo Ho Kim, Daejeon (KR); Seok Ho Jeong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 3 days.

(21) Appl. No.: 15/753,609

(22) PCT Filed: May 17, 2017

(86) PCT No.: PCT/KR2017/005109
§ 371 (c)(1),
(2) Date: Feb. 20, 2018

(87) PCT Pub. No.: WO2017/200292
PCT Pub. Date: Nov. 23, 2017

(65) Prior Publication Data
US 2018/0237614 A1   Aug. 23, 2018

(30) Foreign Application Priority Data

May 18, 2016 (KR) .......... 10-2016-0060831
May 15, 2017 (KR) .......... 10-2017-0059725

(51) Int. Cl.
| | |
|---|---|
| *C08K 5/12* | (2006.01) |
| *C08K 5/101* | (2006.01) |
| *C08L 27/06* | (2006.01) |
| *C08L 25/06* | (2006.01) |
| *C08L 61/02* | (2006.01) |
| *C08L 75/04* | (2006.01) |
| *C07C 69/78* | (2006.01) |
| *C07C 69/82* | (2006.01) |
| *C08K 5/103* | (2006.01) |
| *C07C 69/704* | (2006.01) |
| *C08K 5/11* | (2006.01) |
| *C08L 23/06* | (2006.01) |
| *C08L 23/08* | (2006.01) |
| *C08L 23/12* | (2006.01) |

(52) U.S. Cl.
CPC ............ *C08K 5/12* (2013.01); *C07C 69/704* (2013.01); *C07C 69/78* (2013.01); *C07C 69/82* (2013.01); *C08K 5/101* (2013.01); *C08K 5/103* (2013.01); *C08K 5/11* (2013.01); *C08L 23/06* (2013.01); *C08L 23/0853* (2013.01); *C08L 23/12* (2013.01); *C08L 25/06* (2013.01); *C08L 27/06* (2013.01); *C08L 61/02* (2013.01); *C08L 75/04* (2013.01)

(58) Field of Classification Search
CPC .......... C08K 5/12; C08K 5/101; C08K 5/103; C08K 5/11; C07C 69/704; C07C 69/78; C07C 69/82; C07C 68/82; C08L 23/06; C08L 23/0853; C08L 23/23; C08L 25/06; C08L 27/06; C08L 61/02; C08L 75/04; C08L 23/12
USPC .......................................................... 524/296
See application file for complete search history.

(56) References Cited

U.S. PATENT DOCUMENTS

| | | | |
|---|---|---|---|
| 5,990,214 A * | 11/1999 | Arendt .................... | C07C 69/76 524/296 |
| 8,329,796 B2 | 12/2012 | Grass | |
| 9,534,104 B2 | 1/2017 | Naert et al. | |
| 2010/0305255 A1 | 12/2010 | Grass | |
| 2013/0274395 A1 | 10/2013 | Arendt et al. | |
| 2013/0274396 A1 | 10/2013 | Arendt et al. | |
| 2013/0310473 A1 | 11/2013 | Becker et al. | |
| 2013/0317153 A1 | 11/2013 | Grass et al. | |
| 2014/0096703 A1 * | 4/2014 | Lee ......................... | C08K 5/12 106/505 |
| 2016/0053085 A1 | 2/2016 | Arendt et al. | |
| 2016/0326346 A1 | 11/2016 | Gourdin et al. | |
| 2017/0145187 A1 * | 5/2017 | Pfeiffer ................... | C08K 5/11 |

FOREIGN PATENT DOCUMENTS

| | | | | |
|---|---|---|---|---|
| CN | 101407461 A | * | 4/2009 | |
| CN | 101925571 A | | 12/2010 | |
| CN | 101993548 A | | 3/2011 | |
| CN | 102964626 A | | 3/2013 | |
| CN | 103221467 A | | 7/2013 | |
| CN | 103328202 A | | 9/2013 | |
| CN | 103649196 A | | 3/2014 | |
| CN | 103687732 A | | 3/2014 | |
| CN | 103724857 A | | 4/2014 | |
| EP | 2810932 A1 | | 12/2014 | |
| KR | 10-2010-0116176 A | | 10/2010 | |
| KR | 10-2013-0119947 A | | 11/2013 | |
| KR | 10-2013-0141611 A | | 12/2013 | |
| KR | 10-2015-0123346 A | | 11/2015 | |
| WO | WO-2008140177 A1 | * | 11/2008 | ............. C07C 69/82 |
| WO | 2015/101569 A1 | | 7/2015 | |
| WO | WO-2016005357 A1 | * | 1/2016 | ............... C08K 5/12 |

OTHER PUBLICATIONS

CN 101993548 A, machine translation, EPO espacenet. (Year: 2011).*
CN 101407461 A, machine translation, EPO espacenet. (Year: 2009).*

* cited by examiner

Primary Examiner — Josephine L Chang
(74) Attorney, Agent, or Firm — Morgan, Lewis & Bockius LLP

(57) ABSTRACT

A plasticizer composition, a resin composition and methods of preparing the same are disclosed. The compositions and methods comprise a terephthalate-based material, which has two alkyl groups bound to a diester group, and a dibenzoate-based material. The compositions and methods have a weight ratio of the terephthalate-based material to the dibenzoate-based material of 99:1 to 1:99.

2 Claims, No Drawings

PLASTICIZER COMPOSITION, RESIN COMPOSITION AND METHODS OF PREPARING THE SAME

TECHNICAL FIELD

This application is a National Stage Application of International Application No. PCT/KR2017/005109 filed on May 17, 2017, which claims the benefit of Korean Patent Application No. 10-2016-0060831 filed on May 18, 2016 and Korean Patent Application No. 10- 2017-0059725 filed on May 15, 2017, all of which are hereby incorporated by reference in their entirety for all purposes as if fully set forth herein.

The present invention relates to a plasticizer composition, a resin composition, and methods of preparing the same.

BACKGROUND ART

Conventionally, a plasticizer forms an ester through a reaction between an alcohol and a polycarboxylic acid such as phthalic acid or adipic acid. In addition, in consideration of domestic and international regulations for phthalate-based plasticizers harmful to humans, there is ongoing research on plasticizer compositions that can replace phthalate-based plasticizers such as terephthalate-, adipate-, and other polymer-based plasticizers.

Generally, a plasticizer is used as a material for various products such as electric wires, pipes, flooring materials, wallpaper, sheets, artificial leather, tarpaulins, tape and food wrapping materials obtained in the related industries according to processing methods such as extrusion molding, injection molding, calendering, etc. after suitably adding various additives including resins like polyvinylchloride (PVC), etc., fillers, stabilizers, pigments, anti-fog agents to provide various processing properties.

Meanwhile, there is an increasing demand for environmentally friendly products relating to flooring materials, wallpaper, soft and hard sheets, etc. obtained in the plastisol industry, the calendering industry, the extruding/injecting compound industry, etc., and in order to reinforce quality characteristics, processability and productivity of each end product for such environmentally friendly products, suitable plasticizers have to be used depending on discoloration, migration, mechanical properties, etc.

Depending on properties required by industry in various areas of use, such as tensile strength, an elongation rate, light fastness, a migration property, gelability or an absorption rate, a PVC resin is mixed with a supplementary material such as a plasticizer, a filler, a stabilizer, a viscosity depressant, a dispersant, an antifoaming agent or a foaming agent.

In the current plasticizer market, environmentally-friendly plasticizers are competitively developing in the related field due to environmental issues of phthalate plasticizers, and recently, new products for overcoming inferiority of di(2-ethylhexyl)terephthalate (DEHTP) in qualities such as plasticization efficiency, migration ability, etc., which are being used as general purpose products among such environmentally-friendly plasticizers, have been developed.

Therefore, it is necessary to continue conducting research on technology for developing products with a new composition which has properties superior to those of the DEHTP in order to be optimally applied as a plasticizer for a vinylchloride-based resin.

DISCLOSURE

Technical Problem

Therefore, during research on plasticizers, the inventors developed a plasticizer composition, which can improve inferior properties caused by structural restraints, is environmentally friendly, can be improved in processability due to an improved absorption rate and improved plasticization efficiency, can reduce the total amount of the plasticizer applied due to improved physical properties such as migration and volatile loss, and can have excellent mechanical properties due to improved tensile strength and an improved elongation rate when used in combination with a resin composition, and thus completed the invention.

Technical Solution

In one aspect, the present invention provides a plasticizer composition, which includes a terephthalate-based material having a C9 or C10 alkyl group bound to a diester group; and a dibenzoate-based material including one or more dibenzoate-based compounds represented by Formula 1, in which a weight ratio of the terephthalate-based material to the dibenzoate-based material is 99:1 to 1:99.

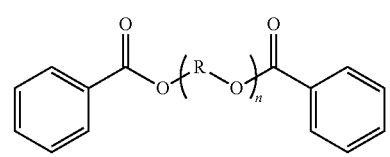

[Formula 1]

In Formula 1, R is a C2 to C4 alkylene group, and n is an integer of 1 to 3. In another aspect, the present invention provides a resin composition which includes 5 to 150 parts by weight of the above-described plasticizer composition with respect to 100 parts by weight of one or more resins selected from the group consisting of ethylene vinyl acetate, polyethylene, polypropylene, polyketone, polyvinyl chloride, polystyrene, polyurethane, and a thermoplastic elastomer.

Advantageous Effects

A plasticizer composition according to an exemplary embodiment of the present invention can be environmentally friendly, can be improved in processability due to an improved absorption rate and improved plasticization efficiency, can reduce the total amount of the plasticizer applied due to improved physical properties such as migration and volatile loss, and can have excellent mechanical properties due to improved tensile strength and an improved elongation rate when used in a resin composition.

MODES OF THE INVENTION

Hereinafter, the present invention will be described in detail.

First, the present invention has a technical feature for providing a plasticizer composition which can improve poor physical properties caused by structural restraints.

According to an exemplary embodiment of the present invention, a plasticizer composition further including a terephthalate-based material may be provided. Particularly, the terephthalate-based material may be contained in a content selected from the ranges of 1 to 99 wt %, 30 to 99 wt %, 40 to 99 wt %, 50 to 95 wt % or 60 to 90 wt % based on the total weight of the plasticizer composition.

For example, the terephthalate-based material may have a terminal group independently selected from alkyl groups having 1 to 12, 3 to 11, 4 to 10, 8 to 10, 8 to 9 or 8 carbon atoms.

However, in the present invention, an alkyl group binding to a diester group of the terephthalate-based material may have 9 or 10 carbon atoms. When there are less than 9 carbon atoms, for example, when a butyl group having 4 carbon atoms is bound to the diester group, volatile loss or migration loss may be at poor levels, and it may be difficult to improve mechanical properties such as a tensile strength or an elongation rate. In addition, even when an octyl group or 2-ethylhexyl group having 8 carbon atoms is bound to the diester group, mechanical properties such as the tensile strength and the elongation rate may be exhibited at unsatisfactory levels. Accordingly, the alkyl group bound to the diester group preferably has 9 or 10 carbon atoms.

The terephthalate-based material may be one or more selected from the group consisting of diisononyl terephthalate (DINTP), diisodecyl terephthalate (DIDTP) and DPHTP.

In addition, according to an exemplary embodiment of the present invention, a plasticizer composition further including a dibenzoate-based material including one or more dibenzoate-based compounds, in addition to the terephthalate-based material, may be provided. The dibenzoate-based compound may be represented by Formula 1 below.

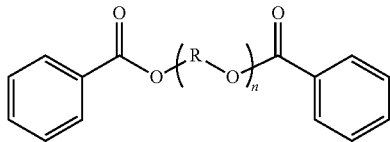

[Formula 1]

In Formula 1, R is an alkylene group having 2 to 4 carbon atoms, and n may be an integer of 1 to 3.

Specifically, the dibenzoate-based compound represented by Formula 1 may be a compound in which an alkylene group and a dibenzoate group are sequentially bound to either side of an ester group which is present in the center. When n is 2 or more, the alkylene groups represented by R may have the same or different number of carbon atoms. Preferably, the same alkylene groups are bound, they have 2 to 4 carbon atoms, and alkyl groups having 1 to 3 carbon atoms may be bound as a branch. When the branches are bound, the carbon number of the branch is preferably smaller than that of the main chain binding to the dibenzoate group.

Here, when n is 2 or more, and the alkylene groups represented by R are the same, the compound of the present invention may be called a non-hybrid dibenzoate-based compound, whereas when n is 2 or more, and the alkylene groups represented by R are different, the compound of the present invention may be called a hybrid dibenzoate-based compound. However, when used as a plasticizer composition, the non-hybrid dibenzoate-based compound may be more common than the hybrid dibenzoate-based compound, and if there is no mention of hybrid or non-hybrid in the specification, every R may be treated as the same non-hybrid dibenzoate-based compound.

In Formula 1, R is preferably any one selected from the group consisting of ethylene, propylene, isopropylene, butylene and isobutylene, but the present invention is not limited thereto. Preferably, the dibenzoate-based compound represented by Formula 1 is diethylene glycol dibenzoate, dipropylene glycol dibenzoate, or triethylene glycol dibenzoate.

A dibenzoate-based material including one or more such dibenzoate-based compounds may be the diethylene glycol dibenzoate, dipropylene glycol dibenzoate, or triethylene glycol dibenzoate, or a mixture thereof, or a mixture further including the dibenzoate-based compound matching the definition of R.

According to an exemplary embodiment of the present invention, the terephthalate-based material and the dibenzoate-based material may be contained in a weight ratio of 99:1 to 1:99 in the plasticizer composition, and the upper limit of the weight ratio range may be 99:1, 95:5, 90:10, 85:15, 80:20, 70:30 or 60:40, and the lower limit thereof may be 1:99, 5:95, 10:90, 15:85, 20:80, 30:70 or 40:60. The range of the weight ratio is preferably 90:10 to 20:80, and more preferably 90:10 to 30:70.

As described in the present invention, when the terephthalate-based material is mixed with the dibenzoate-based material and then applied to a plasticizer composition, the composition may become highly environmentally-friendly, and may be improved in an absorption rate, plasticization efficiency, migration, volatile loss, and physical properties such as tensile strength and elongation rate.

In the present invention, as a method of preparing the plasticizer composition, a blending method may be applied, and an example of the blending method will be described below. Descriptions of the terephthalate-based material and the dibenzoate-based material are the same as described above, and thus will be omitted.

The plasticizer composition may be prepared by preparing the terephthalate-based material and the dibenzoate-based material and blending the terephthalate-based material and the dibenzoate-based material in a specific weight ratio of 99:1 to 1:99. The terephthalate-based material and the dibenzoate-based material may be single compounds, or a mixture.

The terephthalate-based material may be prepared through direct esterification of any one alcohol selected from the group consisting of isononyl alcohol, isodecyl alcohol and 2-propylheptyl alcohol, and terephthalic acid.

The direct esterification may be performed by adding terephthalic acid to an alcohol and then reacting the resulting mixture in the presence of a catalyst under a nitrogen atmosphere; removing an unreacted alcohol and neutralizing an unreacted acid; and performing dehydration and filtration through vacuum distillation.

In addition, the alcohol may be used in the range of 150 to 500 mol %, 200 to 400 mol %, 200 to 350 mol %, 250 to 400 mol %, or 270 to 330 mol % on the basis of 100 mol % of terephthalic acid.

Meanwhile, the catalyst may include, for example, one or more selected from acidic catalysts such as sulfuric acid, hydrochloric acid, phosphoric acid, nitric acid, para-toluenesulfonic acid, methanesulfonic acid, ethanesulfonic acid, propanesulfonic acid, butanesulfonic acid, alkyl sulfate, etc., metal salts such as aluminum sulfate, lithium fluoride, potassium chloride, cesium chloride, calcium chloride, iron chloride, aluminum phosphate, etc., metal oxides such as a heteropolyacid, etc., natural/synthetic zeolites, cation and anion exchange resins, and organic metals such as a tetra alkyl titanate and polymers thereof, etc. As a specific example, the catalyst may be a tetra alkyl titanate.

An amount of the catalyst used may depend on its type, and for instance, the amount of a homogeneous catalyst may be in the range of 0.01 to 5 wt %, 0.01 to 3 wt %, 1 to 5 wt % or 2 to 4 wt % with respect to total 100 wt % of the reactants, and the amount of a heterogeneous catalyst may be in the range of 5 to 200 wt %, 5 to 100 wt %, 20 to 200 wt %, or 20 to 150 wt % with respect to a total amount of the reactants.

The reaction temperature may be 180 to 280° C., 200 to 250° C., or 210 to 230° C.

Alternatively, the terephthalate-based material may be prepared through transesterification which is a reaction of a terephthalate as a starting material with an alcohol.

The "transesterification" used herein refers to a reaction between an alcohol and an ester as shown in Reaction Scheme 1, thereby interchanging R" of the ester and R' of the alcohol as shown in Reaction Scheme 1:

[Reaction Scheme 1]

According to an exemplary embodiment of the present invention, the transesterification may produce three types of ester compositions according to three cases in which an alkoxide of the alcohol attacks carbons of two ester (RCOOR") groups present in an ester-based compound; an alkoxide of the alcohol attacks carbons of one ester (RCOOR") group present in an ester-based compound; and there is no reaction between an alcohol and an ester group in an ester-based compound.

In addition, compared to an acid-alcohol esterification, the transesterification does not cause water contamination, may solve problems caused by the use of an acidic catalyst because of proceeding without a catalyst, and has advantages of reducing byproducts and a reaction time when performed in the presence of a metal catalyst.

For example, when diisononyl terephthalate is prepared by the transesterification between dimethyl terephthalate and isononyl alcohol, diisononyl terephthalate may be obtained with a purity of 98% or higher.

The metal catalyst may be, for example, an organic metal catalyst, a metal oxide catalyst, a metal salt catalyst or a metal itself.

The metal component may be, for example, any one selected from the group consisting of tin, titanium and zirconium or a mixture of two or more thereof.

In addition, after the transesterification, removing of the byproduct such as an ester-based compound, which is generated from the reaction with the unreacted alcohol, by distillation may be further performed in the preparation of the terephthalate-based material.

The direct esterification and the transesterification may also be applied in preparation of the above-described dibenzoate-based material. As such, when the dibenzoate-based material is prepared by direct esterification or transesterification, the same procedures and details as used in the preparation of the terephthalate-based material may be applied.

The plasticizer composition prepared as described above may be included in a range of 5 to 150 parts by weight, 40 to 100 parts by weight, or 40 to 50 parts by weight with respect to 100 parts by weight of a resin selected from the group consisting of ethylene vinyl acetate, polyethylene, polypropylene, polyketone, polyvinyl chloride, polystyrene, polyurethane, and a thermoplastic elastomer, and thus may be applied as a resin composition effective in all of compound, sheet, and plastisol formulations.

For example, the plasticizer composition may be applied in preparation of electric wires, flooring materials, interior materials for automobiles, films, sheets, wall paper or tubes.

EXAMPLES

Hereinafter, to explain the present invention in detail, the present invention will be described in detail with reference to examples. However, examples according to the present invention may be modified in a variety of different forms, and the scope of the present invention should not be construed as being limited to the examples to be described below. The exemplary embodiments of the present invention are provided for those of ordinary skill in the art to more fully understand the present invention.

Preparation Example 1: Preparation of di(2-propylheptyl)terephthalate (DPHTP)

498.0 g of purified terephthalic acid (TPA), 1248 g of 2-propylheptyl alcohol ((2-PH); a molar ratio of TPA:2-EH—(1.0):(3.0)) and 1.54 g of a titanium-based catalyst (tetra isopropyl titanate (TIPT); 0.31 parts by weight with respect to 100 parts by weight of TPA) as a catalyst were added to a 4-neck 3 L reaction vessel equipped with a cooler, a condenser, a decanter, a reflux pump, a temperature controller, an agitator, etc., and a temperature was slowly increased to approximately 170° C. At approximately 170° C., water was generated, and esterification was performed for approximately 4.5 hours while a nitrogen gas was continuously added at a reaction temperature of approximately 220° C. under atmospheric pressure, and then terminated when an acid value reached 0.01.

After the reaction, distillation extraction was performed for 0.5 to 4 hours under reduced pressure to remove unreacted components. To remove unreacted components at a predetermined content or less, steam extraction was performed using steam for 0.5 to 3 hours under reduced pressure, and neutralization was performed using an alkali solution after a reaction solution was cooled to approximately 90° C. Additionally, washing could be performed, and then the reaction solution was dehydrated to remove moisture. Filter mediawere input to the dehydrated reaction solution, stirred for a predetermined time and filtered, thereby finally obtaining 1326.7 g of DPHTP (yield: 99.0%).

Preparation Example 2: Preparation of Diethylene Glycol Dibenzoate (DEGDB)

1221 g of purified benzoic acid (BA) and 530.5 g of diethylene glycol ((DEG) were added at a molar ratio of BA:DEG (2.0):(1.0), and 2.0 g of a titanium-based catalyst (tetraisopropyltitanate (TIPT)) as a catalyst and a small amount of xylene were added to a 4-neck 2 L reaction vessel equipped with a cooler, a condenser, a decanter, a reflux pump, a temperature controller, an agitator, etc., and then a temperature was slowly increased to approximately 170° C. When water was generated at approximately 170° C., the amount of xylene was adjusted to facilitate the removal of the generated water, and the reaction was terminated when the content of an intermediate, a monobenzoate, among the reactants was 5% or less. Afterward, 1,530 g of the final product, DEGDB (yield: 98%) was obtained by a similar method to that described in Preparation Example 1.

Example 1

The DPHTP prepared in Preparation Example 1 and DEGDB were mixed in a weight ratio of 70:30, thereby obtaining a plasticizer composition.

Examples 2 to 6 and Comparative Examples 1 to 3

Examples 2 to 6 and Comparative Examples 1 to 3 were prepared as shown in Table 1.

Below, dipropylene glycol dibenzoate is denoted by "DPGDB," and triethylene glycol dibenzoate is denoted by "TEGDB."

TABLE 1

| | TP-based material | Benzoate-based material | Mixed weight ratio |
|---|---|---|---|
| Example 1 | DPHTP | DEGDB | 7:3 |
| Example 2 | DPHTP | DEGDB | 5:5 |
| Example 3 | DINTP | DEGDB | 8:2 |
| Example 4 | DINTP | DEGDB | 6:4 |
| Example 5 | DIDTP | DPGDB | 8:2 |
| Example 6 | DIDTP | TEGDB | 6:4 |
| Comparative Example 1 | GL300* (DEHTP) | | |
| Comparative Example 2 | DEHTP | DEGDB | 75:25 |
| Comparative Example 3 | DBTP | DEGDB | 6:4 |

*GL300 ™: DEHTP produced by LG Chem Ltd.

Experimental Example 1: Preparation of Samples and Evaluation of Performance

The plasticizers of Examples 1 to 6 and Comparative Examples 1 to 3 were used as experimental samples. For sample preparation, with reference to ASTM D638, 40 parts by weight of the plasticizer and 3 parts by weight of a stabilizer (LOX 912 NP) were mixed with 100 parts by weight of PVC in a mixer, and the resulting mixture was subjected to roll-milling at 170° C. for 4 minutes and pressed for 2.5 minutes (low pressure) and 2 minutes (high pressure) at 180° C., thereby manufacturing 1 T and 3 T sheets. Each sample was subjected to a test for physical properties, and the results are shown in Table 2 below.

<Test Items>
Hardness

According to ASTM D2240, Shore hardness (Shore "D") was measured at 25° C. under conditions of 3 T and 10 s.

Tensile Strength

According to ASTM D638, each specimen was pulled at a cross head speed of 200 mm/min (1 T) using a tester, U.T.M, (Manufacturer; Instron, Model No.; 4466), and a position at which the specimen was broken was detected. A tensile strength was calculated as follows:

Tensile strength (kgf/mm$^2$)=Load value (kgf)/Thickness (mm)×Width (mm)

Measurement of Elongation Rate

According to ASTM D638, each specimen was pulled at a cross head speed of 200 mm/min (1 T) using the U.T.M, and a position at which the specimen was broken was detected. An elongation rate was calculated as follows:

Elongation rate (%)=Length after elongation/Initial length×100

Measurement of Migration Loss

An experimental specimen having a thickness of 2 mm or more was obtained according to KSM-3156, and following attachment of glass plates to both sides of the specimen, a weight of 1 kgf/cm$^2$ was applied to the specimen. The specimen was put in a convection oven (80° C.) for 72 hours, and cooled at room temperature for 4 hours. Then, after the glass plates attached to both sides of the specimen were removed, a weight was measured before and after the glass plate and the specimen plate were put in the oven and thus a migration loss was calculated by the equation as follows:

Migration loss (%)=[(Initial weight of specimen at room temperature−Weight of specimen after being put into oven)/Initial weight of specimen at room temperature]×100

Measurement of Volatile Loss

The prepared specimen was processed at 100° C. for 72 hours, and a weight of the specimen was measured as follows:

Volatile loss (%)=[(Weight of initial specimen−Weight of specimen after processed)/Weight of initial specimen]×100

Measurement of Absorption Rate

An absorption rate was evaluated by measuring the time taken to stabilize the torque of a mixer in which a resin and an ester compound are mixed together using a planetary mixer (Brabender, P600) at 77° C. and 60 rpm.

TABLE 2

| | Hardness (Shore D) | Tensile strength (kg/cm$^2$) | Elongation rate (%) | Migration loss (%) | Volatile loss (%) | Absorption rate (m:s) |
|---|---|---|---|---|---|---|
| Example 1 | 49.0 | 265.4 | 322.1 | 2.56 | 1.12 | 5:40 |
| Example 2 | 47.8 | 260.5 | 320.8 | 2.11 | 0.84 | 5:20 |
| Example 3 | 48.8 | 258.4 | 315.4 | 2.03 | 0.95 | 5:45 |
| Example 4 | 47.5 | 255.0 | 318.6 | 1.86 | 1.18 | 5:10 |
| Example 5 | 48.8 | 262.4 | 332.7 | 2.10 | 0.78 | 5:55 |
| Example 6 | 49.2 | 275.0 | 318.9 | 1.77 | 0.98 | 5:15 |
| Comparative Example 1 | 48.9 | 236.7 | 288.6 | 3.21 | 1.63 | 7:15 |
| Comparative Example 2 | 48.8 | 237.5 | 293.5 | 2.87 | 2.23 | 5:20 |
| Comparative Example 3 | 45.5 | 204.5 | 256.0 | 5.20 | 11.20 | 2:10 |

Referring to Table 2, compared to Examples 1 to 6, it can be confirmed that the elongation rates and the tensile strengths in Comparative Examples 1 to 3 are highly reduced. Specifically, in Comparative Example 2 and Comparative Example 3 which used terephthalate having neither 9 nor 10 carbon atoms, it was seen that the tensile strength and the elongation rate are at least 10% lower than those of the Examples. Particularly, in Comparative Example 3, it can be seen that the volatile loss and the migration loss are considerably low, and it can be inferred that, due to the very high absorption rate, a proper gelling-induction time cannot be ensured, and thus processability is degraded. In addition, in Comparative Example 1 without a dibenzoate-based material, since the absorption rate is very low, a mixing time can be longer or a mixing temperature should be increased, leading to an increase in energy consumption and an adverse influence on processability and a production rate. It can be confirmed that the tensile strength and the elongation rate are also at unsatisfactory levels.

Therefore, it can be confirmed that, when a terephthalate- and a dibenzoate-based materials which are controlled to have 9 or 10 carbon atoms are mixed and applied as a plasticizer, a resin having excellent physical properties can be prepared.

The invention claimed is:

1. A plasticizer composition, wherein plasticizers of the composition consist of:
   di(2-propylheptyl)terephthalate (DPHTP); and
   diethylene glycol dibenzoate (DEGDB);
   wherein
   a weight ratio of DPHTP to DEGDB is 70:30 to 50:50, and
   DEGDB is the only dibenzoate included in the plasticizer composition.

2. A resin composition, comprising:
   100 parts by weight of a polyvinylchloride; and 5 to 150 parts by weight of the plasticizer composition of claim 1.

* * * * *